United States Patent
Sugarman

(10) Patent No.: US 6,726,887 B1
(45) Date of Patent: Apr. 27, 2004

(54) COMPOSITION OF OXIME AND HYDROXY-ESTER FOR THE SOLVENT EXTRACTION OF METALS

(75) Inventor: Alan David Sugarman, Manchester (GB)

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 09/857,766

(22) PCT Filed: Nov. 16, 1999

(86) PCT No.: PCT/GB99/03807

§ 371 (c)(1), (2), (4) Date: Jun. 11, 2001

(87) PCT Pub. No.: WO00/36167

PCT Pub. Date: Jun. 22, 2000

(30) Foreign Application Priority Data

Dec. 12, 1998 (GB) .............................................. 9827288

(51) Int. Cl.⁷ ............................. C01G 3/00; C01G 9/00; C01G 51/00; C01G 53/00
(52) U.S. Cl. ............................. 423/24; 423/99; 423/139; 252/184
(58) Field of Search ............................. 423/24, 99, 139; 252/184

(56) References Cited

U.S. PATENT DOCUMENTS

| | | |
|---|---|---|
| 4,678,563 A | 7/1987 | Keys |
| 5,200,104 A | 4/1993 | Zuerner et al. |
| 5,470,552 A | 11/1995 | Kordosky et al. |
| 5,908,605 A | 6/1999 | Virnig et al. |

FOREIGN PATENT DOCUMENTS

| | | |
|---|---|---|
| EP | 0 202 833 | 11/1986 |
| EP | 0 416 822 | 3/1991 |
| WO | WO 98/28454 | 7/1998 |
| WO | WO 99/10546 | 3/1999 |

Primary Examiner—Steven Bos
(74) Attorney, Agent, or Firm—Pillsbury Winthrop LLP

(57) ABSTRACT

A solvent extraction composition is provided which comprises one or more orthohydroxyarylaldoximes or orthohydroxyarylketoximes and one or more esters substituted with a hydroxyl group, and preferably a water immiscible organic solvent. The orthohydroxyarylaldoximes, or orthohydroxyarylketoximes commonly have Formula (1),

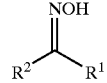

Formula (1)

wherein $R^1$ is hydrogen or a hydrocarbyl group, and $R^2$ is an ortho-hydroxyaryl group; and the esters substituted with a hydroxyl group are of Formula (2),

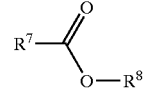

Formula (2)

wherein one of $R^7$ or $R^8$ is a substituted hydrocarbyl group with at least one hydroxyl group and the other is an optionally substituted hydrocarbyl group. Preferred orthohydroxyarylaldoximes are 5-($C_9$ to $C_{14}$ alkyl)-2-hydroxybenzaldoximes and preferred orthohydroxyarylketoximes are 5-($C_9$ to $C_{14}$ alkyl)-2-hydroxyacetophenone oximes. Preferred esters substituted with a hydroxy group are highly-branched alkyl esters comprising from 5 to 51 carbon atoms, wherein the hydroxy group resides on $R^8$. Processes for the extraction of metal values from aqueous acidic and ammoniacal solutions are also provided.

23 Claims, No Drawings

COMPOSITION OF OXIME AND HYDROXY-ESTER FOR THE SOLVENT EXTRACTION OF METALS

This application is the National Phase of International Application PCT/GB99/03807 filed Nov. 16, 1999 which designated the U.S. and that International Application was published under PCT Article 21(2) in English.

The present invention concerns a solvent extraction composition, a solvent extraction process and especially a process for the extraction of metals, particularly copper, from aqueous solutions, especially solutions obtained by leaching ores.

It is known to extract metals, especially copper, from aqueous solutions containing the metal in the form of, for example, a salt, by contacting the aqueous solution with a solution of a solvent extractant in a water immiscible organic solvent and then separating the solvent phase loaded with metal, i.e. containing at least a part of the metal in the form of a complex. The metal can then be recovered by stripping with a solution of lower pH followed for example, by electrowinning. Most commonly, the aqueous metal-containing solutions for extraction are the result of the acid leaching of ores. However it is known that some metals, especially copper, can be leached from certain ores with ammoniacal solutions. This has the advantage that solutions containing especially high concentrations of copper are derived and that there is little contamination of the solution with iron.

Solvent extractants which have found favour in recent years particularly for the recovery of copper from aqueous solutions include oxime reagents, especially o-hydroxyaryloximes and o-hydroxyarylketoximes. Whilst such reagents have been found to work well in the recovery of copper from solutions, one problem which has been encountered in the application of such reagents is that the oxime and ketoxime reagents can strongly bind metals to the extent that the efficiency of metal transfer from leach solution to strip solution can be impaired. In order to overcome such problems, modifiers have been used to effect the binding efficiency of the extractants. Typical modifiers are disclosed in WO96/25525, and in particular a class of highly branched ester modifiers are disclosed in EP-A-0202833. However, as solvent extraction processes are increasingly employed in more diverse situations, there is still a need to identify further modifiers.

According to a first aspect of the present invention, there is provided a solvent extraction composition comprising one or more orthohydroxyarylaldoximes or orthohydroxyarylketoximes, and one or more esters substituted with a hydroxy group.

The compositions preferably also comprise a water immiscible organic solvent.

The orthohydroxyarylaldoxime or orthohydroxyarylketoxime compounds employed in the present invention are substantially water insoluble and preferably have the formula:

Formula (1)

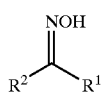

wherein
$R^1$ is hydrogen or an optionally substituted hydrocarbyl group
$R^2$ is an optionally substituted ortho-hydroxyaryl group, and salts thereof.

Whilst the invention is described herein with reference to a compound of Formula (1), it is understood that it relates to said compound in any possible tautomeric forms, and also the complexes formed between orthohydroxyarylaldoximes or orthohydroxyarylketoximes and metals, particularly copper.

Optionally substituted hydrocarbyl groups which may be represented by $R^1$ preferably comprise optionally substituted alkyl and aryl groups including combinations of these, such as optionally substituted aralkyl and alkaryl groups.

Examples of optionally substituted alkyl groups which may be represented by $R^1$ include groups in which the alkyl moieties can contain from 1 to 20, especially from 1 to 4, carbon atoms. A preferred orthohydroxyarylketoxime is one in which $R^1$ is alkyl, preferably containing up to 20, and especially up to 10, and more preferably up to 3 saturated aliphatic carbon atoms, and most preferably $R^1$ is a methyl group.

Examples of optionally substituted aryl groups which may be represented by $R^1$ include optionally substituted phenyl groups. When $R^1$ is an aryl group, it is preferably an unsubstituted phenyl group.

Most preferably $R^1$ represents a hydrogen atom.

Optionally substituted ortho-hydroxyaryl groups which may be represented by $R^2$ include optionally substituted phenols. Examples of optionally substituted phenols which may be represented by $R^2$ include those of formula:

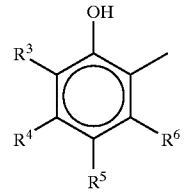

wherein $R^3$ to $R^6$ each independently represent H or a $C_1$ to $C_{22}$, preferably a $C_7$ to $C_{15}$, linear or branched alkyl group. Particularly preferably only $R^5$ represents a $C_{1-22}$ alkyl group, most preferably a $C_7$ to $C_{15}$ alkyl group, with $R^3$, $R^4$ and $R^6$ representing H.

When $R^1$ or $R^2$ is substituted, the substituent(s) should be such as not to affect adversely the ability of the orthohydroxyarylaldoxime or orthohydroxyarylketoxime to complex with metals, especially copper. Suitable substituents include halogen, nitro, cyano, hydrocarbyl, such as $C_{1-20}$-alkyl, especially $C_{1-10}$-alkyl; hydrocarbyloxy, such as $C_{1-20}$-alkoxy, especially $C_{1-10}$-alkoxy; hydrocarbyloxycarbonyl, such as $C_{1-20}$-alkoxycarbonyl, especially $C_{1-10}$-alkoxycarbonyl; acyl, such as $C_{1-20}$-alkylcarbonyl and arylcarbonyl, especially $C_{1-10}$-alkylcarbonyl and phenylcarbonyl; and acyloxy, such as $C_{1-20}$-alkylcarbonyloxy and arylcarbonyloxy, especially $C_{1-10}$-alkylcarbonyloxy and phenylcarbonyloxy. There may be more than one substituent in which case the substituents may be the same or different.

In many embodiments, when an orthohydroxyarylketoxime employed, the orthohydroxyarylketoxime is a 5-($C_8$ to $C_{14}$ alkyl)-2-hydroxyacetophenone oxime, particularly 5-nonyl-2-hydroxyacetophenone oxime.

In many preferred embodiments, when an orthohydroxyarylaldoxime employed, the orthohydroxyarylaldoxime is a 5-($C_8$ to $C_{14}$ alkyl)-2-hydroxybenzaldoxime, particularly 5-nonyl-2-hydroxybenzaldoxime.

The composition may comprise one or more different orthohydroxyarylaldoximes or orthohydroxyarylketoximes or mixtures thereof in which the nature of the substituent groups represented by $R^1$ and $R^2$ differ between component orthohydroxyarylaldoximes or orthohydroxyarylketoximes, especially where the component orthohydroxyarylaldoximes or orthohydroxyarylketoximes are isomeric. Such isomeric mixtures may have better solubility in organic solvents than a single orthohydroxyarylketoxime.

The orthohydroxyarylaldoximes or orthohydroxyarylketoximes are often present in an amount of up to 60% by weight of the composition, commonly no more than 50%, and usually no more than 40% w/w. Often, the orthohydroxyarylaldoxime or orthohydroxyarylketoxime comprises at least 1% by weight, commonly at least 2.5% by weight and usually at least 5% by weight of composition, and preferably comprises from 7.5 to 20%, such as about 10%, by weight of the composition.

The esters substituted with a hydroxy group employed in the present invention are substantially water insoluble and commonly have the formula:

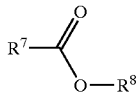

Formula (2)

wherein one of $R^7$ or $R^8$ is a substituted hydrocarbyl group which is substituted with at least one hydroxyl group and the other is an optionally substituted hydrocarbyl group. Preferably, the ester is an aliphatic or aromatic-aliphatic ester, and particularly preferably a branched chain aliphatic or aromatic-aliphatic ester.

The esters substituted with a hydroxy group (hereinafter Hydroxy-esters) which may be employed in this invention may be di-esters or polyesters, but are especially mono-esters.

The Hydroxy-esters of the present invention can contain from 5 to 51 carbon atoms, preferably from 7 to 40 carbon atoms, and more preferably from 9 to 25 carbon atoms.

The Hydroxy-esters are preferably highly branched. In the context of the present invention, "highly branched" means that the ratio of the number of methyl carbon atoms ($CH_3$ groups) to non-methyl carbon atoms (non $CH_3$ groups) is higher than 1:5 and preferably higher than 1:3, and is often less than 1.8:1, preferably less than 1.5:1.

Optionally substituted hydrocarbyl groups which may be represented by $R^7$ and $R^8$ preferably comprise optionally substituted alkyl and aryl groups including combinations of these, such as optionally substituted aralkyl and alkaryl groups.

Examples of optionally substituted alkyl groups which may be represented by $R^7$ and $R^8$ include groups in which the alkyl moieties can contain from 1 to 25, especially from 2 to 12, carbon atoms. When $R^7$ is an optionally substituted alkyl group, it is preferred that it contain up to 12 carbon atoms, more preferably up to 8 carbon atoms, and especially up to 4 carbon atoms. When $R^8$ is an optionally substituted alkyl group, it is preferred that it contain at least 2 carbon atoms, especially at least 4 carbon atoms, and especially at least 6 carbon atoms.

Examples of optionally substituted aryl groups which may be represented by $R^7$ and $R^8$ include optionally substituted phenyl groups. In certain embodiments, only one of $R^7$ or $R^8$ is an aryl group. It is especially preferred, when only one of $R^7$ and $R^8$ is an aryl group, that $R^7$ is an aryl group. When $R^7$ or $R^8$ is an aryl group, it is preferably an unsubstituted phenyl group.

The Hydroxy-esters must contain a hydroxy group but optionally may contain other functional groups. Functional groups which may be present include halogen, nitro, cyano, hydrocarbyl, such as $C_{1-20}$-alkyl, especially $C_{1-10}$-alkyl; hydrocarbyloxy, such as $C_{1-20}$-alkoxy, especially $C_{1-10}$-alkoxy; hydrocarbyloxycarbonyl, such as $C_{1-20}$-alkoxycarbonyl, especially $C_{1-10}$-alkoxycarbonyl; acyl, such as $C_{1-20}$-alkylcarbonyl and arylcarbonyl, especially $C_{1-10}$-alkylcarbonyl and phenylcarbonyl; and acyloxy, such as $C_{1-20}$-alkylcarbonyloxy and arylcarbonyloxy, especially $C_{1-10}$-alkylcarbonyloxy and phenylcarbonyloxy. There may be more than one functional group in which case the functional groups may be the same or different.

The hydroxy group that must be present in the Hydroxy-esters of this invention may reside on the portion of the Hydroxy-ester nominally derived from an alcohol (the optionally substituted hydrocarbyl group $R^8$) or a carboxylic acid (the optionally substituted hydrocarbyl group $R^7$). It is preferred that the hydroxy group reside on the portion of the Hydroxyester derived from an alcohol, and that particularly this portion is derivable from a diol. It is especially preferred that the hydroxy group is attached to an aliphatic portion of the Hydroxy-ester.

Where the Hydroxy-ester is a product of the reaction of an alcohol and a hydroxy substituted mono-carboxylic acid, it is preferred that the alcohol is an alkyl alcohol and comprises from 2 to 12 carbon atoms, and the acid is a hydroxy substituted alkyl carboxylic acid and comprises from 2 to 12 carbon atoms. Where the Hydroxy-ester is a product of the reaction of a diol and a mono-carboxylic acid, it is preferred that the diol is an alkyl diol and comprises at least 6 carbon atoms, and the mono-carboxylic acid comprises from 2 to 12 carbon atoms. Examples of useful esters include 2,2dimethyl-1,3-propanediol mono-isobutyrate, 2-hydroxymethyl-2-methylpentanol mono-tertpentanoate and nonane-1,3-diol mono-acetate, and particularly 2,2,4-trimethyl-1,3-pentanediol mono-isobutyrate and 2,2,4-trimethyl-1,3-pentanediol monobenzoate.

The Hydroxy-esters often comprise up to 30% w/w of the composition, preferably from 0.1 to 20% w/w, and most preferably from 0.5 to 15% w/w. The weight ratio of Hydroxy-ester to aldoxime or ketoxime is often in the range of from 10:1 to 1:10, commonly from 5:1 to 1:5, and preferably from 1:1 to 1:4.

Organic solvents which may be present in the composition include any mobile organic solvent, or mixture of solvents, which is immiscible with water and is inert under the extraction conditions to the other materials present Examples of suitable solvents include aliphatic, alicyclic and aromatic hydrocarbons and mixtures of any of these as well as chlorinated hydrocarbons such as trichloroethylene, perchloroethylene, trichloroethane and chloroform. Examples of suitable hydrocarbon solvents include ESCAID 110, ESCAID 115, ESCAID 120, ESCAID 200, and ESCAID 300 commercially available from Exxon (ESCAID is a trade mark), SHELLSOL D70 and D80 300 commercially available from Shell (SHELLSOL is a trade mark), and CONOCO 170 commercially available from Conoco (CONOCO is a trade mark). Certain suitable solvents have a low aromatic (<1% w/w) content, for example hydrocarbon solvents such as ESCAID 110 commercially available from Exxon (ESCAID is a trade mark), and ORFOM SX 10 and ORFOM SX11 commercially available from Phillips Petroleum (ORFOM is a trade mark). Preferred solvents are hydrocarbon solvents including high flash point solvents with a high aromatic content such as SOLVESSO 150 commercially available from Exxon (SOLVESSO is a trade mark) and includes solvents which consist essentially of a mixture of trimethylbenzenes such as AROMASOL H, commercially available from Imperial Chemical Industries PLC (AROMASOL is a trade mark). Especially preferred, however, on grounds of low toxicity and wide availability are hydrocarbon solvents of relatively low aromatic content such as kerosene, for example ESCAID 100 which is a petroleum distillate with a total aromatic content of 23% commercially available from Exxon (ESCAID is a trade mark), or ORFOM SX7, commercially available from Phillips Petroleum (ORFOM is a trade mark).

In many embodiments, the composition comprises at least 30%, often at least 45% by weight, preferably from 50 to 95% w/w of water-immiscible hydrocarbon solvent.

Certain preferred compositions comprise at least one orthohydroxyarylaldoxime or orthohydroxyarylketoxime which may be present in an amount up to 42% w/w, and preferably from 7.5 to 20% w/w, and at least one Hydroxy-ester which may also be present in an amount up to 28%, preferably from 0.5 to 15%, w/w. Compositions comprising at least one orthohydroxyarylaldoxime or orthohydroxyarylketoxime which is present in an amount from 7.5 to 20% w/w and at least one Hydroxy-ester which is present in an amount of from 0.5 to 15% w/w are particularly preferred.

Particularly preferred solvent extraction compositions are those comprising from 7.5 to 20% w/w of 5-($C_8$ to $C_{14}$ alkyl)-2-hydroxyacetophenone oxime or 5-($C_8$ to $C_{14}$ alkyl)-2-hydroxybenzaldoxime, 0.5 to 15% w/w of 2,2,4-trimethyl-1,3-pentanediol mono-isobutyrate or benzoate, and from 65 to 92% of water-immiscible hydrocarbon solvent.

Advantageously, it may be preferred to make and supply the composition in the form of a concentrate. In certain embodiments, the concentrate may consist of a mixture of one or more orthohydroxyarylaldoximes or orthohydroxyarylketoximes, and one or more Hydroxy-esters (ie no solvent is present). The concentrate may then be diluted by the addition of organic solvents as described herein above to produce compositions in the ranges as described herein above. Where the concentrate contains a solvent, it is preferred that the same solvent is used to dilute the concentrate to the "in use" concentration range. In many embodiments, the concentrate composition comprises up to 30%, often up to 20% by weight, preferably up to 10% w/w of water-immiscible hydrocarbon solvent. Often the concentrate composition comprises greater than 5% w/w of water-immiscible hydrocarbon solvent.

If desired, compounds or mixtures of compounds selected from the group consisting of alkylphenols, alcohols, esters, ethers, polyethers, carbonates, ketones, nitriles, amides, carbamates, sulphoxides, and salts of amines and quaternary ammonium compounds may also be employed as additional modifiers in the composition of the invention. Particularly preferred are mixtures comprising a first compound selected from the group consisting of alkylphenols, alcohols, esters, ethers, polyethers, carbonates, ketones, nitriles, amides, carbamates, sulphoxides, and salts of amines and quaternary ammonium compounds and a second compound selected from the group consisting of alkanols having from 6 to 18 carbon atoms, an alkyl phenol in which the alkyl group contains from 7 to 12 carbon atoms, and tributylphosphate.

The aforementioned additional modifiers may be used in the preparation of extractant compositions containing one or more orthohydroxyarylaldoximes or orthohydroxyarylketoximes, one or more esters substituted with a hydroxyl group, one or more additional modifiers and a water immiscible organic solvent.

According to a second aspect of the present invention, there is provided a process for the extraction of a metal from solution in which an acidic solution containing a dissolved metal is contacted with a solvent extraction composition comprising a water immiscible organic solvent and a water-immiscible solvent extractant, whereby at least a fraction of the metal is extracted into the organic solution, characterised in that the solvent extraction composition comprises one or more orthohydroxyarylaldoximes or orthohydroxyarylketoximes and one or more esters substituted with a hydroxyl group.

Metals that may be extracted in the process according to the second aspect of the present invention include copper, cobalt, nickel, manganese and zinc, most preferably copper. The orthohydroxyarylaldoxime, orthohydroxyarylketoxime, esters substituted with a hydroxyl group, and water immiscible organic solvent are as herein described before. It is preferred that there is predominance of orthohydroxyarylaldoximes in relation to any orthohydroxyarylketoximes present in the solvent extraction composition. It is especially preferred that the solvent extraction composition comprises one or more orthohydroxyarylaldoximes and one or more esters substituted with a hydroxyl group.

The aqueous acidic solution from which metals are extracted by the process of the second aspect of the present invention often has a pH in the range of from −1 to 7, preferably from 0 to 5, and most preferably from 0.25 to 3.5. Preferably, when the metal to be extracted is copper pH values of less than 3 chosen so that the copper is extracted essentially free of iron, cobalt or nickel. The solution can be derived from the leaching of ores or may be obtained from other sources, for example metal containing waste streams such as from copper etching baths.

The concentration of metal, particularly copper, in the aqueous acidic solution will vary widely depending for example on the source of the solution. Where the solution is derived from the leaching of ores, the metal concentration is often up to 75 g/l and most often from 1 to 40 g/l. Where the solution is a waste stream, the metal concentrations are often somewhat higher than those from the leaching of ores, for example up to 150 g/l, usually from 75 to 130 g/l.

Preferred solvent extraction compositions are those aldoxime containing compositions as discussed above with respect to the first aspect of the present invention.

The process of the second aspect of the present invention can be carried out by contacting the solvent extractant composition with the aqueous acidic solution. Ambient or elevated temperatures, such as up to 75° C. can be employed if desired. Often a temperature in the range of from 5 to 60° C., and preferably from 15 to 40° C., is employed. The aqueous solution and the solvent extractant are usually agitated together to maximise the interfacial areas between the two solutions. The volume ratio of solvent, extractant to aqueous solution are commonly in the range of from 20:1 to 1:20, and preferably in the range of from 5:1 to 1:5. In many embodiments, to reduce plant size and to maximise the use of solvent extractant, organic to aqueous volume ratios close to 1:1 are employed, such as 1.5:1 or less.

The mole ratio of the total of orthohydroxyarylaldoxime and/or orthohydroxyarylketoxime present to copper transferred is often selected to be in the range of from 2.7:1 to 1:1. Preferably, to achieve improved hydrometallurgical properties, such as reduced viscosity arid improved phase disengagement, the mole ratio of oxime to copper transferred is from 2.3:1 to 2.0:1.

After contact with the aqueous acidic solution, the metal can be recovered from the solvent extractant by contact with an aqueous acidic strip solution.

The aqueous strip solution employed in the process according to the second aspect of the present invention is usually acidic, commonly having a pH of 2 or less, and preferably a pH of 1 or less, for example, a pH in the range of from −1 to 0.5. The strip solution commonly comprises a mineral acid, particularly sulphuric acid, nitric acid or hydrochloric acid. In many embodiments, acid concentrations, particularly for sulphuric acid, in the range of from 130 to 200 g/l and preferably from 150 to 180 g/l are employed. A low acid concentration but at least 4M chloride containing strip solution as described in European Patent application no. 93301095.1 (publication no. 0 562 709 A2) or International application publication No. WO95/04835 (both of which are incorporated herein by reference) can be employed. When the extracted metal is copper or zinc, preferred strip solutions respectively comprise stripped or spent electrolyte from a copper or zinc electro-winning cell, typically comprising up to 80 g/l copper or zinc, often greater than 20 g/l copper or zinc and preferably from 30 to 70 g/l copper or zinc, and up to 220 g/l sulphuric acid, often greater than 120 g/l sulphuric acid, and preferably from 150 to 180 g/l sulphuric acid.

The volume ratio of organic solution to aqueous strip solution in the process of the second aspect of the present invention is commonly selected to be such so as to achieve transfer, per liter of strip solution, of up to 50 g/l of metal, especially copper into the strip solution from the organic solution. In many industrial copper electrowinning processes transfer is often from 10 g/l to 35 g/l, and preferably from 15 to 20 g/l of copper per liter of strip solution is transferred from the organic solution. Volume ratios of organic solution to aqueous solution of from 1:2 to 15:1 and preferably from 1:1 to 10:1, especially less than 3:1 are commonly employed.

A preferred embodiment of the second aspect of the present invention comprises a process for the extraction of a metal from aqueous acidic solution in which:

in step 1, a water-immiscible solvent extraction composition comprising an orthohydroxyarylaldoxime and one or more esters substituted with a hydroxyl group is first contacted with the aqueous acidic solution containing metal, in step 2, separating the solvent extraction composition containing metal-solvent extractant complex from the aqueous acidic solution;

in step 3, contacting the solvent extraction composition containing metal-solvent extractant complex with an aqueous acidic strip solution to effect the stripping of the copper from the water immiscible phase;

in step 4, separating the metal-depleted solvent extraction composition from the loaded aqueous strip solution.

According to a third aspect of the present invention, there is provided a process for the extraction of a metal from solution in which an aqueous ammoniacal solution containing a dissolved metal is contacted with a solvent extraction composition comprising a water immiscible organic solvent and a water-immiscible solvent extractant, whereby at least a fraction of the metal is extracted into the organic solution, characterised in that the solvent extraction composition comprises one or more orthohydroxyarylaldoximes or orthohydroxyarylketoximes and one or more esters substituted with a hydroxyl group.

Metals that may be extracted in the process according to the third aspect of the present invention include copper, cobalt, nickel, manganese and zinc, most preferably copper.

The orthohydroxyarylaldoxime, orthohydroxyarylketoxime, esters substituted with a hydroxyl group and water immiscible organic solvent are as herein described before. It is preferred that there is predominance of orthohydroxyarylketoximes in relation to any orthohydroxyarylaldoximes present in the solvent extraction composition. It is especially preferred that the solvent extraction composition comprises one or more orthohydroxyarylketoxime and one or more esters substituted with a hydroxyl group.

The aqueous ammoniacal solution from which metals are extracted by the process of the third aspect of the present invention often has a pH in the range of from 7 to 12, preferably from 8 to 11, and most preferably from 9 to 10. The solution can be derived from the leaching of ores, particularly chalcocite ores, or may be obtained from other sources, for example metal containing waste streams such as from copper etching baths.

Preferred solvent extraction compositions are those ketoxime containing compositions as discussed above with respect to the first aspect of the present invention.

The concentration of metal, particularly copper, in the aqueous ammoniacal solution will vary widely depending for example on the source of the solution. Where the solution is derived from the leaching of ores, the metal concentration is often up to 75 g/l and most often from 10 to 40 g/l. Where the solution is a waste stream, the metal concentrations are often somewhat higher than those from the leaching of ores, for example up to 150 g/l, usually from 75 to 130 g/l.

The process of the third aspect of the present invention can be carried out by contacting the solvent extractant composition with the aqueous ammoniacal solution. Ambient or elevated temperatures, such as up to 75° C. can be employed if desired. Often a temperature in the range of from 15 to 60° C., and preferably from 30 to 50° C., is employed. The aqueous solution and the solvent extractant are usually agitated together to maximise the interfacial areas between the two solutions. The volume ratio of solvent extractant to aqueous solution are commonly in the range of from 20:1 to 1:20, and preferably in the range of from 5:1 to 1:5. In many embodiments, to reduce plant size and to maximise the use of solvent extractant, organic to aqueous volume ratios close to 1:1 are employed, such as 1.5:1 or less, and preferably 1.3:1 or less.

The mole ratio of the combined orthohydroxyarylaldoxime and orthohydroxyarylketoxime present to copper transferred is often selected to be in the range of from 2.7:1 to 1:1. Preferably, to achieve improved hydrometallurgical properties, such as reduced viscosity and improved phase disengagement, the mole ratio of oxime to copper transferred is from 2.3:1 to 2.0:1.

After contact with the aqueous ammoniacal solution, the metal can be recovered from the solvent extractant by contact with an aqueous strip solution having a pH lower than that from which the metal was extracted.

The aqueous lower pH strip solution employed in the process according to the third aspect of the present invention is usually acidic and is as described for the strip solution in the process of the second aspect of the present invention. When the extracted metal is copper or zinc, preferred strip solutions respectively comprise stripped or spent electrolyte from a copper or zinc electro-winning cell, typically comprising up to 80 g/l copper or zinc, often greater than 40 g/l copper or zinc and preferably from 50 to 70 g/l copper or zinc, and up to 220 g/l sulphuric acid, often greater than 120 g/l sulphuric acid, and preferably from 150 to 180 g/l sulphuric acid.

The volume ratio of organic solution to aqueous strip solution in the process of the third aspect of the present invention is commonly selected to be such so as to achieve transfer, per liter of strip solution, of up to 50 g/l of metal, especially copper into the strip solution from the organic solution. In many industrial copper electrowinning processes transfer is often from 10 g/l to 35 g/l, and preferably from 15 to 20 g/l of copper per liter of strip solution is transferred from the organic solution. Volume ratios of organic solution to aqueous solution of from 1:2 to 15:1 and preferably from 1:1 to 10:1, especially less than 3:1 are commonly employed.

A preferred embodiment of the third aspect of the present invention comprises a process for the extraction of a metal from aqueous ammoniacal solution in which:

in step 1, a water-immiscible solvent extraction composition comprising an orthohydroxyarylketoxime and one or more esters substituted with a hydroxyl group is first contacted with the aqueous ammoniacal solution containing metal, in step 2, separating the solvent extraction composition containing metal-solvent extractant complex from the aqueous ammoniacal solution;

in step 3, contacting the solvent extraction composition containing metal-solvent extractant complex with an aqueous strip solution of lower pH than the ammoniacal solution to effect the stripping of the copper from the water immiscible phase;

in step 4, separating the metal-depleted solvent extraction composition from the lower pH aqueous solution.

The metal can be recovered from the aqueous strip solution by conventional methods, for example by electrowinning.

The invention is further illustrated, but not limited, by the following examples.

EXAMPLE G NERAL M THODS

Each modifier was tested with the same oxime to determine the amount of modifier required to achieve a target minimum strip level under given strip conditions. These target levels were chosen based on experience of the performance of commercial extractants under such conditions. For the three aqueous strip solutions (compositions in parenthesis) the target minimum strip levels were 1.8 gpl Cu (30 gpl Cu/120 gpl $H_2SO_4$), 1.6 gpl Cu (30 gpl Cu/150 gpl $H_2SO_4$) and 1.24 gpl Cu (30 gpl Cu/180 gpl $H_2SO_4$). Then using the concentrations of modifier defined by the target minimum strip level experiment, a maximum load value was determined under fixed loading conditions. Then finally by performing a strip experiment on the maximum load solutions, and calculating the difference between the loaded and stripped copper values, a net copper transfer value was derived for each modifier under fixed extract and strip conditions.

Modifier Concentration Required to Achieve Target Minimum Strip Value

Sample Solutions

5-Nonyl-2-hydroxybenzaldoxime (hereinafter "oxime") (100 g) was dissolved in the hydrocarbon solvent commercially available under the trade name ORFOM SX7 (1 l) to give a 100 g/l stock solution. Then for each modifier to be tested, four separate aliquots (25 ml) of the stock solution were removed and these were used to prepare the test solutions as follows:

1) To the first aliquot (25 ml) of stock solution was added 2.5 g modifier and the resulting solution was then diluted to 50 ml by the addition of ORFOM SX7. This gave a 50 g/l oxime, 50 g/l modifier test solution.

2) To the second aliquot (25 ml) of stock solution was added 1.5 g modifier and the resulting solution was then diluted to 50 ml by the addition of ORFOM SX7. This gave a 50 g/l oxime, 30 g/l modifier test solution.

3) To the third aliquot (25 ml) of stock solution was added 0.75 g modifier and the resulting solution was then diluted to 50 ml by the addition of ORFOM SX7. This gave a 50 g/l oxime, 15 g/l modifier test solution.

4) To the first aliquot (25 ml) of stock solution no modifier was added, the solution was only diluted to 50 ml by the addition of ORFOM SX7. This gave a 50 g/l oxime, no modifier test solution.

Evaluation Procedure

For each of the modifiers, the four test solutions were each evaluated by stripping with three copper/acid strip solutions. For this procedure, three aliquots (10 ml) of each test solution were removed separately. Each aliquot was then loaded to equilibrium with $Cu^{2+}$ by shaking the test aliquot with an equal volume (1:1 O/A (organic/aqueous)) of an aqueous $CuSO_4$ solution comprising 10 g/l $Cu^{2+}$ buffered at pH4.5 for two minutes in a separating funnel, discarding the aqueous phase and repeating with fresh copper solution three further times. Once loaded with copper, each organic phase was isolated and then stripped of copper. Stripping of each solution was carried out by shaking the test aliquot with an equal volume of a given strip solution for two minutes in a separating funnel, discarding the aqueous phase and repeating with fresh strip solution three further times. Aqueous strip solutions consisting of 30 gpl Cu/120 gpl $H_2SO_4$, 30 gpl Cu/150 gpl $H_2SO_4$ and 30 gpl Cu/180 gpl $H_2SO_4$ were used for these evaluations. The copper concentration of the resulting organic phases were determined by atomic absorpton spectroscopy. In total twelve measurements were made for each modifier tested.

The data gathered for each of the strip solutions employed was plotted to give a curve showing copper left in the organic phase post stripping versus concentration of modifier required. This was then used to determine the required amount of each modifier to achieve the target minimum strip level under each of the stripping conditions.

Net Copper Transfer

Test Solutions

Three test solutions were prepared for each modifier containing 50 g/l oxime and modifier at the concentration determined to achieve the target minimum strip values. These were prepared from aliquots (25 ml) of stock solution (nonylsalicylaldoxime (100 g) dissolved in ORFOM SX7 (1l) to give a 100 g/l stock solution) and by adding the required amount of modifier then diluting to 50 ml by the addition of ORFOM SX7.

Evaluation Procedure

Maximum Load Value

Aliquots (10 ml) of each test solution were removed separately and each loaded to equilibrium with copper by contacting with an aqueous $CuSO_4$ solution comprising 5 g/l $Cu^{2+}$ at 1:1 O/A by shaking 4 times for 2 min in a separating funnel with fresh loading solution. Copper loading solutions of pH 1.0, 1.5 and 2.0 were used in the evaluation. Five loaded organic solutions were prepared for each modifier, one at pH 1.0, one at pH 1.5 and three at pH 2.0. The organic layers were separated and filtered through phase separation media before being analysed for copper content by atomic absorption spectroscopy.

Strip Value

The three organic solutions for each modifier loaded at pH 2.0 were then stripped, a different strip condition being used for each. Stripping was carried out at 1:1 O/A by contacting an aliquot (5 ml) of the loaded organic solution with aqueous strip solutions comprising 30 gpl Cu/120 gpl $H_2SO_4$, 30 gpl Cu/150 gpl $H_2SO_4$ or 30 gp Cu/180 gpl $H_2SO_4$ (contact was by shaking 4 times for 2 min in a separating funnel with fresh strip solution). Copper stripping was determined by measuring copper levels in the organic phase by atomic absorption spectroscopy.

As the minimum stripping that can be achieved by the strip conditions is independent of the load conditions, the Net Copper Transfer for a combination of load and strip conditions was determined for each modifier/oxime composition by subtracting the Strip Value for a given strip solution from the Load Value at a given pH.

Example 1

The following results were obtained for the Hydroxyester, 2,2,4-trimethyl-1,3-pentanediol mono-isobutyrate.

The levels of modifier required to achieve the target minimum strip values were 27 gpl (30/180), 33 gpl (30/150) and 38 gpl (30/120).

Using these modifier concentrations a matrix of net copper transfer values under the given pH loading conditions and the strip conditions were generated and are shown in Table 1.

TABLE 1

| gpl modifier | pH1-30/120 | pH1-30/150 | pH1-30/180 | pH1.5-30/120 | pH1.5-30/150 | pH1.5-30/180 | pH2-30/120 | pH2-30/150 | pH2-30/180 |
|---|---|---|---|---|---|---|---|---|---|
| 27 | 3.09 | 3.54 | 3.96 | 3.68 | 4.19 | 4.55 | 3.83 | 4.28 | 4.7 |
| 33 | 3.33 | 3.72 | 4.1 | 3.99 | 4.38 | 4.765 | 4.07 | 4.46 | 4.845 |
| 38 | 3.405 | 3.775 | 4.11 | 4.155 | 4.525 | 4.86 | 4.325 | 4.695 | 5.03 |

Comparative Example A

The following results were obtained for a known commercial modifier 2,2,4-trimethyl-1,3-pentanediol di-isobutyrate.

The levels of modifier required to achieve the target minimum strip values were 41 gpl (30/180), 48 gpl (30/150) and 55 gpl (30/120).

Using these modifier concentrations a matrix of net copper transfer values under the given pH loading conditions and the strip conditions were generated and are shown in Table 2.

TABLE 2

| gpl modifier | pH1-30/120 | pH1-30/150 | pH1-30/180 | pH1.5-30/120 | pH1.5-30/150 | pH1.5-30/180 | pH2-30/120 | pH2-30/150 | pH2-30/180 |
|---|---|---|---|---|---|---|---|---|---|
| 41 | 2.71 | 3.26 | 3.66 | 3.53 | 4.08 | 4.48 | 3.65 | 4.2 | 4.6 |
| 48 | 2.925 | 3.425 | 3.725 | 3.675 | 4.17 | 4.475 | 3.85 | 4.35 | 4.65 |
| 55 | 3.08 | 3.58 | 3.88 | 3.85 | 4.35 | 4.65 | 4 | 4.5 | 4.8 |

The results show that less 2,2,4-trimethyl-1,3-pentanediol mono-isobutyrate (a modifier according to the present invention) is required to achieve the minimum strip value. Furthermore, a point by point comparison of the data presented for each modifier, shows that under each set of load/strip conditions, not only is less Hydroxy-ester modifier required, a higher Net Copper Transfer is achieved and hence the composition of the present invention is a more effective copper transfer agent than the comparative commercial composition.

I claim:

1. A solvent extraction composition comprising one or more orthohydroxyarylaldoximes or orthohydroxyarylketoximes and one or more esters substituted with a hydroxy group, wherein the esters substituted with a hydroxy group are compounds of formula (2):

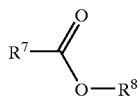

Formula (2)

wherein one of $R^7$ or $R^8$ is a substituted hydrocarbyl group with at least one hydroxyl group and the other is an optionally substituted hydrocarbyl group.

2. A composition according to claim 1, additionally comprising a water immiscible organic solvent.

3. A composition according to claim 1, wherein the orthohydroxyarylaldoxime or orthohydroxyarylketoxime is a compound represented by the Formula (1),

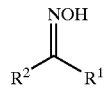

Formula (1)

wherein,
$R^1$ is hydrogen or an optionally substituted hydrocarbyl group
$R^2$ is an optionally substituted ortho-hydroxyaryl group, and salts thereof.

4. A composition according to claim 1, wherein the orthohydroxyarylketoxime is a 5-($C_9$ to $C_{14}$ alkyl)-2-hydroxyacetophenone oxime.

5. A composition according to claim 1, wherein the orthohydroxyarylaldoxime is a 5-($C_9$ to $C_{14}$ alkyl)-2-hydroxybenzaldoxime.

6. A composition according to claim 4 wherein the orthohydroxyarylketoxime is 5-nonyl-2-hydroxy-acetophenone oxime.

7. A composition according to claim 5 wherein the orthohydroxyarylaldoxime is 5-nonyl-2-hydroxy-benzaldoxime.

8. A composition according to any one of claims 1, 2, 3, 4, 5, 6 or 7, wherein the ester substituted with a hydroxy group comprises a highly-branched hydroxy-ester comprising from 9 to 25 carbon atoms.

9. A composition according to any one of claims 1, 2, 3, 4, 5, 6 or 7, wherein the hydroxy functionality of the ester substituted with a hydroxy group resides on $R^8$, and where $R^8$ is branched aliphatic group.

10. A composition according to any one of claims 1, 2, 3, 4, 5, 6 or 7, wherein the ester substituted with a hydroxy group is 2,2,4-trimethyl-1,3-pentanediol mono-isobutyrate or 2,2,4-trimethyl-1,3-pentanediol monobenzoate.

11. A process for the extraction of a metal from solution in which either an acidic solution containing a dissolved metal an aqueous ammoniacal solution containing a dissolved metal is contacted with a solvent extraction composition comprising a water immiscible organic solvent and a water-immiscible solvent extractant, whereby at least a fraction of the metal is extracted into the solvent extraction composition wherein the solvent extraction composition comprises one or more orthohydroxyarylaldoximes or orthohydroxyarylketoximes and one or more esters substituted with a hydroxy group, wherein the esters substituted with a hydroxy group are compounds of formula (2):

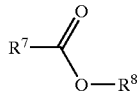

Formula (2)

wherein one of $R^7$ or $R^8$ is a substituted hydrocarbyl group with at least one hydroxyl group and the other is an optionally substituted hydrocarbyl group.

12. A process according to claim 11 wherein there is a predominance of orthohydroxyarylaldoximes in relation to any orthohydroxyarylketoximes present in the solvent extraction composition.

13. A process according to claim 11 wherein there is a predominance of orthohydroxyarylketoximes in relation to any orthohydroxyarylaldoximes present in the solvent extraction composition.

14. A process according to claim 11, wherein the metal is copper, zinc, cobalt or nickel.

15. A process according to claim 11, wherein the ortho-hydroxyaryl oxime or orthohydroxyazylketoxime is selected from the class of compounds represented by the Formula (1),

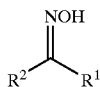

Formula (1)

wherein $R^1$ is hydrogen or an optionally substituted hydrocarbyl group $R^2$ is an optionally substituted ortho-hydroxyaryl group, and salts thereof.

16. A process according to claim 11, wherein the ortho-hydroxyarylketoxime is a 5-($C_9$ to $C_{14}$ alkyl)-2-hydroxyacetophenone oxime.

17. A process according to claim 11, wherein the ortho-hydroxyarylaldoxime is a 5-($C_9$ to $C_{14}$ alkyl)-2-hydroxybenzaldoxime.

18. A process according to any one of claims 11, 13, 14, 15, 16 or 17, wherein the ester substituted with a hydroxy group comprises a highly-branched hydroxy-ester comprising from 9 to 25 carbon atoms.

19. A process according to any one of claims 11, 13, 14, 15, 16 or 17, wherein the hydroxy functionality of the ester substituted with a hydroxy group resides on $R^8$, and where $R^8$ is a branched aliphatic group.

20. A process according to any one of claims 11, 13, 14, 15, 16 or 17, wherein the ester substituted with a hydroxy group is 2,2,4-trimethyl-1,3-pentanediol mono-isobutyrate or 2,2,4-trimethyl-1,3-pentanediol monobenzoane.

21. A process according to claim 14 wherein the metal is copper.

22. A process according to claim 16 wherein the ortho-hydroxyarylketoxime is 5-nonyl-2-hydroxy-acetophenone oxime.

23. A process according to claim 17 wherein the ortho-hydroxyarylaldoxime is 5-nonyl-2-hydroxy-benzldoxime.

* * * * *